(12) United States Patent
Knothe Tate et al.

(10) Patent No.: US 8,609,132 B2
(45) Date of Patent: Dec. 17, 2013

(54) FLOW DIRECTING MATERIALS AND SYSTEMS

(75) Inventors: Melissa Knothe Tate, Cleveland Heights, OH (US); Eric Anderson, Hermitage, PA (US)

(73) Assignee: Case Western Reserve University, Cleveland, OH (US)

( * ) Notice: Subject to any disclaimer, the term of this patent is extended or adjusted under 35 U.S.C. 154(b) by 1195 days.

(21) Appl. No.: 12/106,748

(22) Filed: Apr. 21, 2008

(65) Prior Publication Data

US 2009/0053109 A1    Feb. 26, 2009

Related U.S. Application Data

(60) Provisional application No. 60/913,058, filed on Apr. 20, 2007.

(51) Int. Cl.
*A61L 15/16* (2006.01)
*A61L 15/42* (2006.01)

(52) U.S. Cl.
USPC ............................ 424/445; 424/446; 424/447

(58) Field of Classification Search
USPC .................................................. 424/445–449
See application file for complete search history.

(56) References Cited

U.S. PATENT DOCUMENTS

| | | | |
|---|---|---|---|
| 2002/0082540 A1* | 6/2002 | Johnston et al. | 602/48 |
| 2007/0009582 A1* | 1/2007 | Madsen et al. | 424/445 |

* cited by examiner

*Primary Examiner* — Michael G Hartley
*Assistant Examiner* — Micah-Paul Young
(74) *Attorney, Agent, or Firm* — Tarolli, Sundheim, Covell & Tummino LLP

(57) ABSTRACT

A flow directing material includes a substrate. The substrate includes a first region that exudes fluid under a compressive or tensile load and a second region that imbibes fluid under the compressive or tensile load. The first region has a first porosity and a first permeability and the second region has a second porosity and a second permeability. The first permeability and the second permeability are about $10^{-13}$ $m^2$ to $10^5$ $m^2$. The first porosity and the second porosity are about 0.3 to about 0.7. The first porosity and the second porosity are at least about 5% different.

33 Claims, 3 Drawing Sheets

FLOW DIRECTING MATERIALS AND SYSTEMS

RELATED APPLICATION

This application claims priority from U.S. Provisional Application No. 60/913,058, filed Apr. 20, 2007, the subject matter, which is incorporated herein by reference.

FIELD OF THE INVENTION

The present application relates to flow directing materials and systems, and to the use of the flow directing materials and systems in fluid directing devices, articles, and microfluidic switch systems.

BACKGROUND

Fluid management significantly affects many aspects of health care and is involved in many medical procedures. For example, wound care typically involves absorbing and/or draining wound exudates, blood, serum and other body fluids from the patient. Surgical procedures often create wounds requiring tissue management and fluid drainage. For example, skin grafts have exudates and bleeding that requires management at both the donor and graft sites. However, current tissue management and fluid drainage procedures are often ineffective in maintaining optimum moisture content for promoting wound healing. Excessive drying can lead to desiccation. Excessive moisture, on the other hand, can lead to maceration. Reepithelialization interference, tissue breakdown and necrosis can result therefrom.

Various types of porous, absorbent dressing materials have been used for dressing wounds to accumulate body fluids. The dressing materials facilitate drainage and also the collection and disposal of fluids. A disadvantage with many conventional dressings is that they require changing in order to reduce the risk of infection and to maintain effectiveness. Dressing changes can add significantly to treatment costs and are associated with patient discomfort and medical risks such as infection and damage to reepithelialized tissues. Accordingly, vacuum sources have been employed to drain wounds. For example, Zamierowski U.S. Pat. Nos. 4,969,880; 5,100,396; 5,261,893; 5,527,293 and 6,071,267 pertain to wound dressings, fluid connections, fastening systems and medical procedures utilizing same in connection with vacuum-assisted wound drainage, and are incorporated herein by reference.

Wound treatment procedures can include diffusing wound sites with liquids to flush contaminants, counter infection, promote healing growth and anesthetize the wound. Prior art fluid delivery systems include a device for treating tissues disclosed in the Svedman U.S. Pat. No. 4,382,441; a product and process for establishing a sterile area of skin disclosed in the Groves U.S. Pat. No. 3,367,332; and the transdermal infusion device disclosed in the Westin U.S. Pat. No. 4,605,399. Equipment has also been available which flushes and collects contaminants from wounds.

SUMMARY OF THE INVENTION

The present invention relates to a flow directing material that comprises a substrate. The substrate includes a first region that exudes fluid under a compressive or tensile load and a second region that imbibes fluid under the compressive or tensile load. The first region has a first porosity and a first permeability, and the second region has a second porosity and a second permeability. The first permeability and the second permeability are about $10^{-13}$ m$^2$ to about $10^5$ m$^2$. The first porosity and the second porosity are about 0.3 to about 0.7. The first porosity and the second porosity are at least about 5% different. The flow directing material can be provided in at least one of an absorbent article, textile, drug delivery device, bioprosthetic device, biomaterial implant, or microfluidic device.

In an aspect of the invention, the first region can include a first fluid that can flow from the first region under the compressive or tensile load. The first region can be in contact with a fluid source. The fluid source can be imbibed by the second region under the compressive or tensile load.

The first region and the second region can extend from a first surface of the substrate. Under the compressive or tensile load to the substrate, the first region can exude fluid from the first surface toward the direction of the load, and the second region can imbibe fluid from the first surface away from the direction of the load. The direction of flow of fluid through the first region at the first surface can be opposite to the direction of flow of fluid though the second region at the first surface.

The substrate can also include a second surface substantially opposite to and separated from the first surface. The first region and the second region can be laterally spaced in the substrate and extend between the first surface and the second surface.

In an aspect of the invention, the first region can comprise a first porous polymeric material having a first porosity, and the second region can comprise a second porous polymeric material having a second porosity different that the first porosity. The first porous polymeric material can have a first flexible polymeric foam structure of interconnected open cells, and the second porous polymeric material can have a second flexible polymeric foam structure of interconnected open cells. The stiffness of the first polymeric material and the second polymeric material can determine the penetration depth of the fluid from the first region and to the second region.

In another aspect of the invention, the first region can have a permeability different than the permeability of the second region. The flow directing material can include a porous membrane provided on the first surface of the substrate to modulate fluid flow through the first surface.

In a further aspect of the invention, the substrate can include a plurality of first regions laterally spaced from one another in the substrate and separated by the second region. At least some of the first regions can have a different porosity, volume, volumetric permeability, and/or surface permeability than the porosity, volume, volumetric permeability, and/or surface permeability of the other first regions.

The present invention also relates to a wound dressing. The dressing can comprise a substrate that includes a plurality of first regions that exude fluid under a compressive or tensile load and a plurality of second regions that imbibe fluid under the compressive or tensile load. The first regions can have a first porosity and a first permeability. The second regions can have a second porosity and a second permeability. The first permeability and the second permeability can be about 10-13 m2 to about 105 m2. The first porosity and the second porosity can be about 0.3 to about 0.7. The first porosity and the second porosity are at least about 5% different.

The substrate of the dressing can include a first surface and a second surface separated from the first surface. The first regions and the second regions can extend between the first surface and the second surface. Under the compressive or tensile load to the substrate, the first region can exude fluid from the first surface toward the direction of the load, and the second region can imbibe fluid from the first surface away from the direction of the load.

The first regions of the dressing can include a therapeutic fluid. The therapeutic fluid can flow from the first regions through the first surface when the dressing is under compression. The therapeutic fluid can include at least one pharmaceutical agent, anti-inflammatory agent, antibiotic, antifungal agent, antipathogenic agent, antiseptic agent, hemostatic agents, local analgesics, immunosuppressive agents, growth factor, peptide, or gene therapy agent. The second regions can absorb excess fluid or exudate from a wound of a subject when the first surface of the dressing is applied against the wound.

The first regions of the dressing can comprise a first porous polymeric material having a first porosity. The second regions can comprise a second porous polymeric material having a second porosity different than the first porosity. The first porous polymeric material can have a first flexible polymeric foam structure of interconnected open cells. The second porous polymeric material can have a second flexible polymeric foam structure of interconnected open cells. At least some of the first regions can have a different porosity, volume, volumetric permeability, and/or surface permeability than the porosity, volume, volumetric permeability, and/or surface permeability of other first regions.

In an aspect of the invention, the dressing can include a slip layer attached to the second surface. The slip layer can minimize friction of the outer surface of the dressing when the dressing is applied to the subject.

The present invention further relates to a microfluidic system that includes a first dashpot with a first volume in fluid communication with a second dashpot with a second volume via a fluid communication channel. The ratio of the first volume to the second volume can be about 0.3 to about 2.3. The second volume is at least about 5% less than the first volume. A first fluid channel is in fluid communication with the first dashpot. A second fluid channel is in fluid communication with the second dashpot. A fluid is provided in the first dashpot, the second dashpot, the first channel, the second channel, and the communication channel. A first plunger and a second plunger can displace fluid, respectively, in the first dash pot and the second dashpot. Compression that results in substantially equal displacement of the first plunger in the first dashpot and the second plunger in the second dashpot can result in unequal relative changes in fluid volume (greater relative change in the volume of the first dashpot compared to that of the second dashpot), further resulting in a pressure difference between dashpots and causing fluid to flow from the second dashpot to the first dashpot. Upon substantially equal and opposite displacement of the plunger, resulting in relaxation of the first plunger and the second plunger, fluid flows in the opposite direction, from the first dashpot and the second dashpot through, respectively the first channel and the second channel. In an aspect of the invention, the first dashpot and the second dashpot can have, respectively, a first permeability and a second permeability. The first permeability and the second permeability can be about $10^{-13}$ $m^2$ to about $10^5$ $m^2$.

In an aspect of the invention, a material can be provided in the dashpot that has a particular permeability and porosity, where the system function is to drive a microfluidic device.

In another aspect of the invention, the microfluidic system can be provided as a valve for a lab on-a-chip or provided in a pressure sensor or strain gauge.

DETAILED DESCRIPTION

The present invention relates to a flow directing material and system that can be used, for example, in molecular delivery devices and microfluidic systems. The flow directing material and system of the present invention can optimize anistropic properties of the material and the system to allow for counterintuitive flow in the material and system when the material and system are subjected to compression, a load causing compression, tensile stress, tension or expansion of fluid volume. The anistropic properties of the flow directing material and system are optimized to mimic the relationship between stiffness and permeability coefficients shown to produce counterintuitive fluid flow in bone.

Figures 1A, 1B:
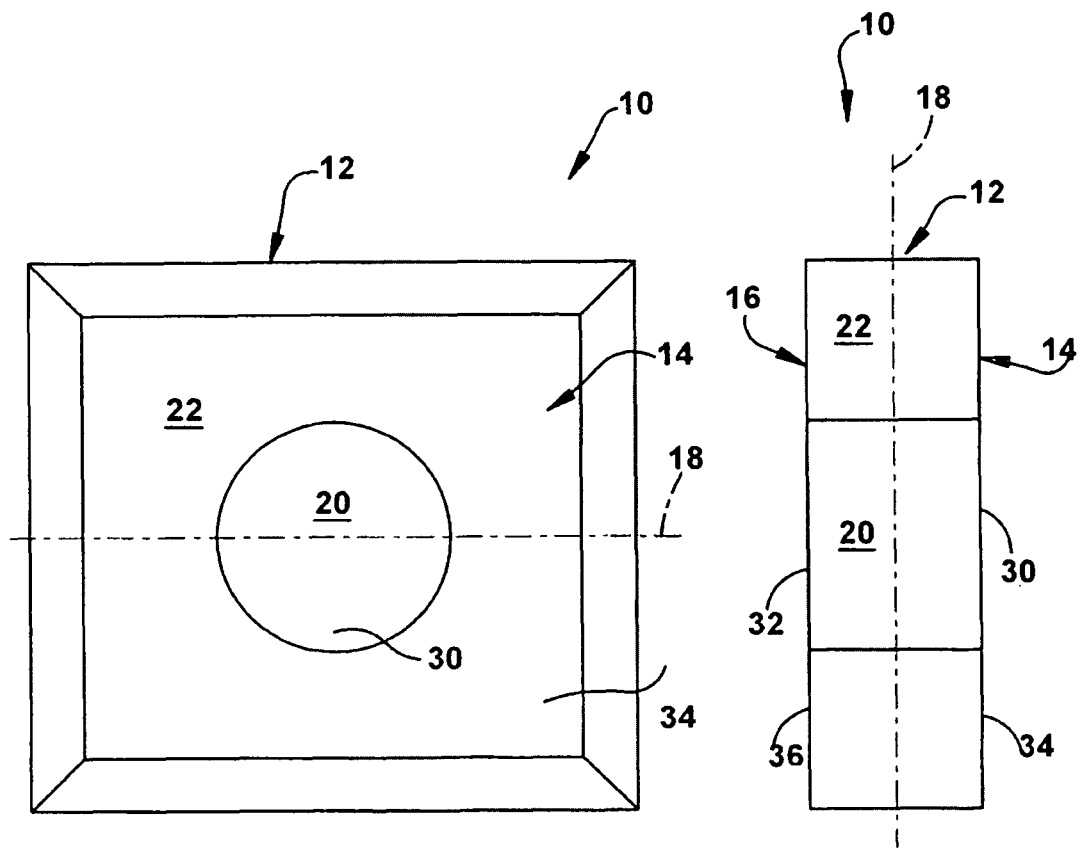
FIG. 1 illustrates a flow directing material in accordance with an aspect of the invention.

FIG. 1 is a schematic illustration of a flow directing material 10 in accordance with one aspect of the invention. The flow directing material 10 includes a porous substrate 12 that is capable of being compressed when a load is applied to the substrate 12. By way of example, the porous substrate can be formed of a porous compliant polymeric foamed material, a porous compliant nano-engineered material, and/or a porous compliant biological material.

The substrate 12 includes a first region 20 that can exude fluid and a second region 22 that can imbibe fluid when the first region 20 and the second region 22 are compressed or a load causing compression is applied to the substrate 12. The first region 20 extends between a first surface 14 and a second surface 16. The first surface 14 can be substantially parallel to the second surface 16 and extend substantially parallel to an axis 18. The first surface 14 and the second surface 16 are illustrated as being substantially flat but need not be depending on the specific application of the flow directing material 10.

The first region defines a first exuding surface 30 on the first surface 14 and a second exuding surface 32 on the second surface 16. The first region can include a fluid depot (not shown) for storing fluid (not shown) that is to be exuded from the first region 20 or the fluid can be dispersed within the first region 20. The first region 20 is illustrated as having a cylindrical shape, but can have other shapes as well as other sizes depending on the use of the flow directing material 10.

The second region 22 also extends between the first surface 14 and the second surface 16. The second region 22 is adjacent to the first region 20. The second region 22 defines a first imbibing surface 34 on the first surface 14 and a second imbibing surface 36 on the second surface 16. Although the second region 22 is illustrated as surrounding the first region 20, the second region 22 need not surround the first region 20 and can be merely adjacent to or abut the first region 20.

The first region 20 and the second region 22 can have, respectively, a first porosity and second porosity. The porosities (or porosity ratio (e.g., void volume of the respective region in mm3/total volume of the respective region in mm3)) of the first region 20 and second region 22 are about 0.3 and about 0.7. The porosities of the first region (i.e., exude region) and the second region (i.e., imbibe region) are also at least about 5% different so that the direction of fluid flow in and/or through the first region 20 will be opposite or contrary to the fluid flow in and/or through the second region 22.

The difference of porosities of the first region 20 and the second region 22 determines the direction of flow of fluid in and/or through the first region 20 and the second region 22. As long as the first region 20 has a porosity at least about 5% different than the second region 22, the flow of fluid in and/or through the first region 20 will be contrary to or opposite the flow of fluid in and/or through the second region 22 when the first region 20 and second region 22 are compressed. In accordance with this aspect, the first region 20 can have a porosity that is at least about 5% lower than the porosity of the second region 22 so that under compression, the first region 20 exudes fluid and the second region 22 imbibes fluid. By way of example, the first region 20 can have a porosity of about 0.3 and the second region 22 can have a porosity of about 0.7

The first region 20 and the second region 22 also have, respectively, a first permeability and a second permeability. The permeabilities of first region 20 and the second region 22 are about are about $10^{-13}$ m$^2$ to about $10^5$ m$^2$. The permeability controls the magnitude of fluid flow in the flow directing material 10 when the flow directing material 10 is under compression and can potentially control the timing of transport of fluid depending on the specific application of the flow directing material 10. In one aspect, the first region 20 can have substantially the same permeability as the second region 22. In another aspect, the first region 20 and the second region 22 can have different permeabilities.

Additionally, the first region 20 and the second region 22, have, respectively, a first stiffness and a second stiffness. The stiffnesses (as well as thicknesses) of the first region 20 and the second region 22 controls the penetration depth of fluid exchange with the surrounding environment. In one aspect, the first region 20 can have substantially the same stiffness as the second region 22. In another aspect, the first region 20 and the second region 22 can have different stiffnesses.

The flow directing material 10 can exude fluid form the first exuding surface 30 and imbibe fluid from the first imbibing surface 34 when a load is applied against the first surface 14 so as to compress the flow directing material 10. The exudation and imbibement of, respectively, the first region 20 and the second region 22 can occur in the direction of the load, e.g., toward or away from the load, so that the first region 20 exudes fluid toward or against the direction of the load and the second region 22 imbibes fluid away from or with the direction of the load. The load or compression need not occur substantially normal to the axis for the first region 20 to exude fluid and the second region 22 to imbibe fluid. The load can be applied at any angle relative to the axis as long as the flow directing material 10 is compressed.

The load need not be compressive but can also be tensile. Tensile loads can be applied, for example, in a plane extending substantially parallel to the axis 18 resulting in a shortening pore heights in accordance with Poisson's effect. In addition to this effect, tensile loads can be applied normal to the surface, which would expand pore volumes, resulting in equal but opposite flows for areas of exudation and imbibition, for a tensile load that is equal but opposite to a given compressive load.

In an aspect of the invention, the first region 20 and the second region 22 can be formed from flexible or compliant polymeric foams having, respectively, a first porosity and a second porosity. The polymeric foams can include those that are substantially open-celled. The cells in such substantially open-celled foam structures can have intracellular openings or windows that are large enough to permit ready fluid transfer from one cell to the other within the regions. These substantially open-celled foam regions will generally have a reticulated character with the individual cells being defined by a plurality of mutually connected, three dimensionally branched webs. The strands of polymeric material making up these branched webs can be referred to as "struts." For purposes of the present invention, a foam material is "open-celled" if at least about 50% of the cells in the foam structure are in fluid communication with at least one adjacent cell.

The polymers used to form the polymeric foam can comprise any polymer that is capable of being foamed or provided with an open-celled structure. Examples of polymers that can be used to form the polymeric foam include elastomers, expanded polytetrafluoroethylene, polypropylene, nylon, hydrophilic polystyrene foams, styrene butadiene styrene, methyl vinyl ether, maleic anhydride, GoreTex, and biopolymers, such as collagen, collagen modified with chondroitin sulfate, cellulose, hydroxypropyl methylcellulose, ethyl cellulose, and chitin.

In one example, the polymeric foam used to form the first region 20 and the second region 22 can comprise a foamed thermoplastic elastomer. The thermoplastic elastomer can be foamed with a foaming agent. The foaming agent used to foam the thermoplastic elastomer can include, for example, a chemical foaming agent that upon exposure to an elevated temperature higher than the melting temperature of the elastomer undergoes a chemical reaction to produce a gas. The chemical foaming agent can be an endothermic chemical foaming agent, an exothermic chemical foaming agent, or a mixture of an endothermic chemical foaming agent and an exothermic chemical foaming agent. The endothermic chemical foaming agent can, for example, comprises a carbonate and an organic acid that reacts chemically with the carbonate to form carbon dioxide, such as a hydrotalcite compound. The exothermic chemical foaming agent can include, for example, azo compounds, such as azodicarbonamide and modifications or derivatives thereof that on decomposition yield nitrogen, carbon monoxide, and carbon dioxide.

By way of example, the flow directing material can be formed from the thermoplastic elastomer using an injection molding process. The elastomer and chemical foaming agent can mixed and heated and then injected into a mold. The mold can include an outer warmer region and inner cooler region that allows the injected elastomer to foam and expand more in the outer region than the inner region and provide the outer region with a greater porosity than the inner region. The outer region can have a porosity of about 0.7 and the inner region can have a porosity of about 0.3.

It will be appreciated that the flow directing material can be formed from other flexible or compliant materials besides polymeric foams. These other materials can include, for example, nano-scale, meso-scale, or micro-scale engineered composites or matrices in which the porosity and the permeability of the composite is controlled as well as biological materials with native or engineered porosities and permeabilities.

Figures 2A, 2B:
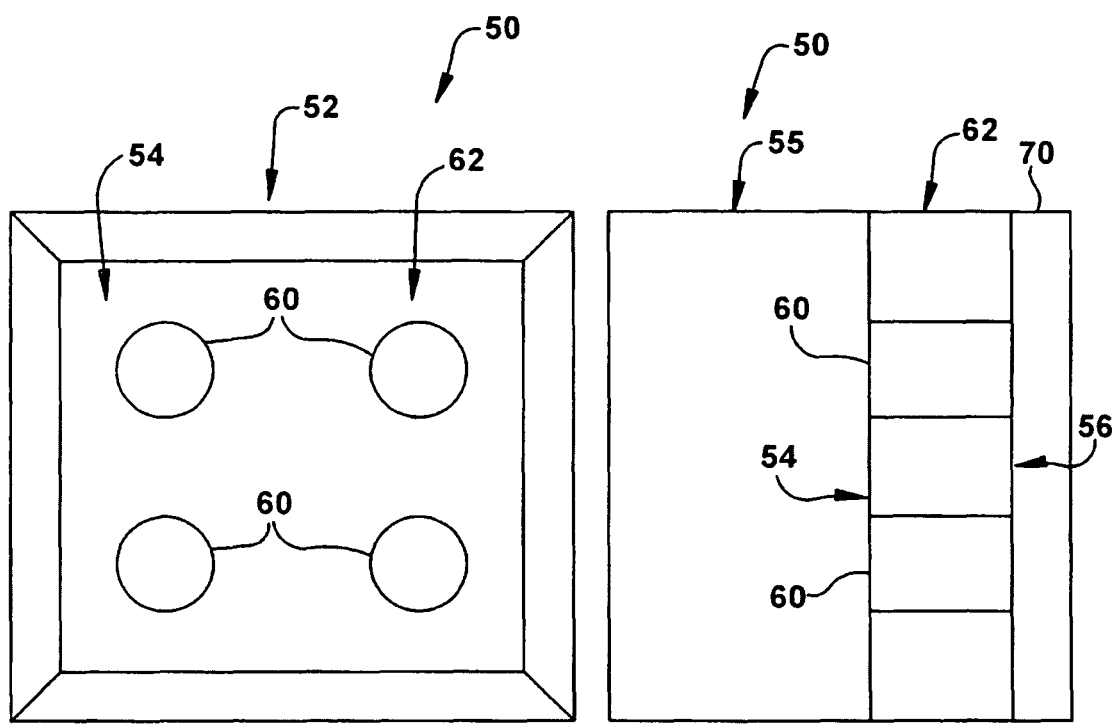
FIG. 2 illustrates a flow directing material in accordance with an aspect of the invention.

The flow directing material can be used in a variety of articles or apparatuses where it is desirable to regulate fluid flow. In one aspect of the invention, the flow directing material can be used to form a wound dressing that both imbibes excess fluid or exudate from a wound and exudes therapeutic agents to the wound when the dressing is under compression. FIG. 2A illustrates one unit of a composite wound dressing 50 in accordance with an aspect of the invention. The composite wound dressing 50 includes a substrate 52 with a delivery surface 54 that can be positioned against a patient's wound or skin 55 and an outer surface 56 that faces away from the patient's wound or skin. The substrate 52 includes a plurality of laterally spaced exuding regions 60 in the form of cylindrical dots that under compression exude a therapeutic fluid. The material 62 surrounding the dots 60 can imbibe excess fluid or exudate when the dressing 50 is compressed against the wound. The exuding regions 60 have a first porosity and a first permeability. The imbibing surrounding region 62 has a second porosity and a second permeability. The first permeability and the second permeability are about $10^{-13}$ m$^2$ to about $10^5$ m$^2$. The first porosity and the second porosity are about 0.3 to about 0.7. The first porosity and the second porosity are at least about 5% different. By way of example, the first porosity is about 0.3, the second porosity is about 0.7, and the first and second permeability are about $10^{-10}$ m$^2$.

The exuding regions 60 of the dressing can include a therapeutic fluid contained in depots (not shown) in the exuding regions 60. The therapeutic fluid can flow from the exuding regions 60 through the delivery surface 54 when the dressing 50 is under compression. The therapeutic fluid can include at least one pharmaceutical agent, anti-inflammatory agent, antibiotic, antifungal agent, antipathogenic agent, antiseptic agent, hemostatic agents, local analgesics, immunosuppressive agents, growth factor, peptide, or gene therapy agent. The second imbibing region 62 can imbibe excess fluid or exudate from the wound or skin of the subject when the delivery surface 54 of the dressing 50 is applied against the wound or skin of the subject and compressed.

The exuding regions 60 of the dressing 50 can comprise a first porous polymeric material having a first porosity. The surrounding imbibing region 62 can comprise a second porous polymeric material having a second porosity different that the first porosity. The first porous polymeric material can have a first flexible polymeric foam structure of interconnected open cells. The second porous polymeric material can have a second flexible polymeric foam structure of interconnected open cells.

The dressing 50 can also include a slip layer 70 attached to the outer surface 56 of the substrate 52. The slip layer 70 can minimize friction of the dressing 50 with the outer environment when the dressing 50 is applied to a wound of the subject.

The composite dressing 50 can deliver therapeutic substances through the delivery dots 62 and imbibe fluid through the surrounding material 62 surrounding the dots 60. The composite dressing 50 can also be designed and/or deliver substances through the larger volume material surrounding the dots and imbibe fluid through the smaller volume of the dots.

FIG. 2B illustrates computational fluid dynamics (CFD) models showing mechanism of action with time lapse, $t_{1-10}$ (B) and control of flow direction (exuding, C, and imbibing, D) through definition of regional porosity and permeability. In the computer model, porosity and permeability of the material comprising the dots and the material surrounding are defined prior to application of a compressive load. Under load, delivery dots exude fluid and the surrounding material imbibes fluid as per design specifications; this effect persists, with dampening, over ten time steps (e.g. seconds, FIG. 2B). The direction and rate of drug delivery (FIG. 2C, dot exudation and surrounding imbibement, magnitude is plotted on a color scale and flow direction is shown by vector plots) and/or moisture wicking (FIG. 2D, dot imbibement and surrounding exudation, magnitude plotted as color, direction as vector) can be controlled precisely through choice of material parameters (FIG. 2C,D) including porosity ratio (dot:surroundings) and permeability. Penetration depth of fluid exchange into the surrounding environment (path length of deliverance and/or imbibement) can be controlled by the stiffness and/or thickness of the material.

Thus, through specific combinations of porosity and permeability, not only can concomitant molecular delivery and moisture wicking be achieved, but also dual molecular delivery/absorption can be achieved by design of dual exuding/imbibing structures with convection parameters tuned for optimal kinetics of each respective molecule.

It will be appreciated that the functionality of delivery dots and imbibement in surrounding areas can be reversed, to accommodate larger depots for substance to be delivered and smaller reservoirs for wicking.

It will also be appreciated that films or layers can also be applied on the delivery surface to modulate flow through the surface of the material/device. Sealant films can have discontinuities with free spaces for dots and/or surrounding areas, allowing for free flow through those areas. In addition, film penetrability can be defined to better control the dynamics of flow (delivery, imbibement) through the surface.

It will further be appreciated, that at least some of the exuding regions can have a different porosity, volume, volumetric permeability, and/or surface permeability than the porosity, volume, volumetric permeability, and/or surface permeability than other exuding regions for complex single molecule release kinetics, dual molecule delivery, and/or fine tuning of imbibement.

The flow directing material of the present invention can also be used for other articles or applications where it is desirable to regulate fluid flow through a material that is under compression or a load. These other articles or applications can include, for example: bandages, including adhesive bandages; absorbent articles, such as diapers, for imbibing bodily fluid while delivering agents (e.g., aloe vera); textiles including but not limited to sport clothing, health textiles, shoe insoles, and seat covers; motor vehicle tires that imbibe water upon contact with the road and route water back to the road; and dual acting cleaning devices for uptake of toxic materials and dirt concomitant to delivery of water, polish, and surface protectors, as well as for use in eco-disasters to mop up/contain oil, toxins, while delivering pH regulating chemicals, buffers, and other agents.

Other applications of the flow directing material can include biomaterial applications. Such biomaterial applications can include, for example: tissue augmentation applications or tissue replacement applications, such as bone grafts and cortical tissue replacement materials; drug eluting stents or grafts; drug eluting patches or membranes, mechanoactive membranes for surgical reconstruction, and any other biomaterial application where a porous material is used, a fluid exchange material is used, or where the material serves a mechanical function while delivering molecular agents. Still other biomaterial application can specifically include those where propylene or GoreTex is used (e.g., an implantable membrane for a hernia sling).

Figure 3:
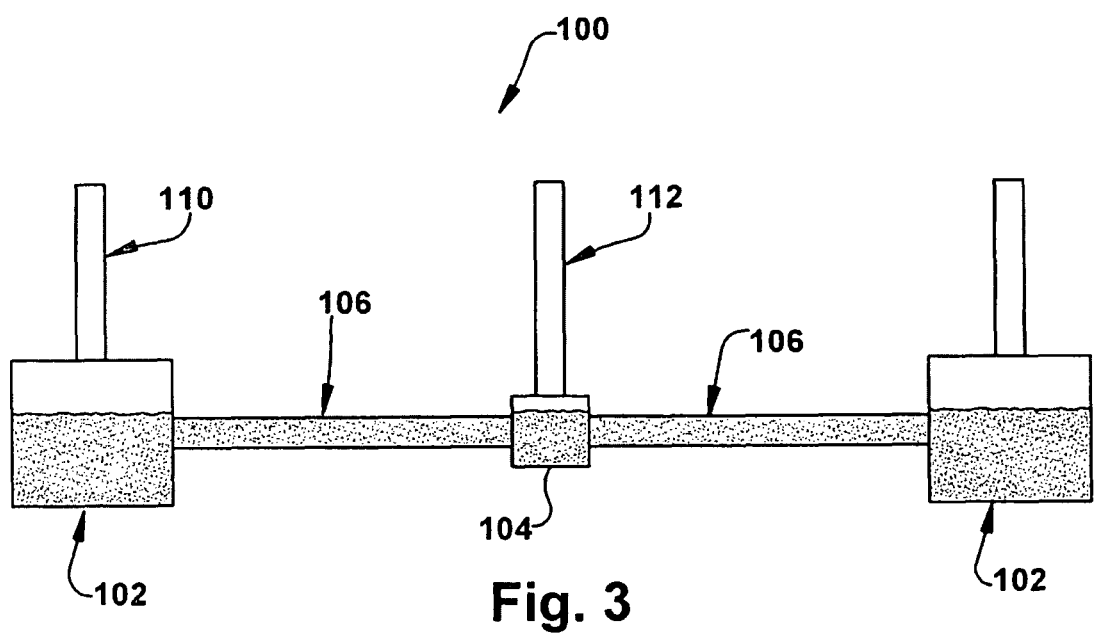
FIG. 3 illustrates a microfluidic system in accordance with an aspect of the invention.

The present invention further relates to a microfluidic system that can be used, for example, as a microfluidic switch. FIG. 3 is a cross-sectional view of an example of a microfluidic system 100 in accordance with an aspect of the invention.

The microfluidic system 100 includes a first dashpot with a first volume 102 in fluid communication with a second dashpot 104 with a second volume that is smaller than the first dashpot 102. The first dashpot 102 and the second dashpot 104 are connected via a fluid communication channel 106.

A first fluid channel 110 is in fluid communication with the first dashpot 102. A second fluid channel 112 is in fluid communication with the second dashpot 104. A fluid 120 is provided in the first dashpot 102, the second dashpot 104, the first channel 110, the second channel 112, and the communication channel 106. A first plunger (not shown) and a second plunger (not shown) can displace fluid, respectively, in the first dash pot 102 and the second dashpot 104.

In an aspect of the invention, the first dashpot 102 and the second dashpot 104 can have, respectively, a first permeability and the second permeability. The first permeability and the second permeability can be about $10^{-13}$ m$^2$ to $10^5$ m$^2$. The ratio of the first volume to second volume is about 0.3 to about 2.3, with the second volume being at least about 5% smaller. The relevant volume ratios are based on the delivery dot: imbibement volume properties, e.g. 0.3-0.7 ratios (2.3×0.3) ratios described above.

The direction of fluid flow in the microfluidic system 100 is controlled by the relative volumes of dashpots 102 and 104. Key to the mechanism is the control of the displacement of the first plunger and the second plunger. Each plunger is displaced the same distance, resulting in pressure differences between dashpots due to the relative volume differences of the dashpots.

Displacement of the first plunger and the second plunger results in an immediate pressure difference between the first dashpot 102 and the second dashpot 104, causing fluid flow through the fluid communication from the smaller second dashpot 104 to the larger volume first dashpots 102. Upon equal relaxation of the first plunger and the second plunger fluid flows from the first dashpot 102 and the second dashpot 104 through, respectively the first channel 110 and the second channel 112.

Displacement of stroke of the first plunger and the second plunger drives the relative differences in flow through the system. The effect persists from as low as 1% displacement (percent of total height), with no observable upward bound, although efficiency/feasibility of the effect are better for lower displacements.

It will be appreciated that none of these effects are limited to compression or decrease in fluid volume which results in pressure differences that drive fluid flow. Another implementation is under tension, resulting in an increase in fluid volume, which at the same magnitude (but opposite direction) of a given compressive force, will result in equal but opposite flow effects predicted for imbibing and exuding structures The microfluidic system can be formed using standard processing techniques used in the fabrication of semiconductor devices and micro-electrical mechanical systems. In one example, the microfluidic system can be formed by providing a substrate layer, such as a silicon substrate (e.g., a single crystal silicon or epitaxial silicon) or wafer, forming an etch stop layer over the wafer (e.g., by chemical vapor deposition), and then forming a second layer over the etch stop layer (e.g., by spin-on-glass techniques). The first dashpot, the second dashpot can then be formed in the second layer by, for example, providing a patterned photoresist over the second layer and anistropically etching the second layer. A third layer can then be provide over the etched second layer and etched to form the first channel and the second channel. Plungers having equal volumes can then be provided to increase or decrease the volumes of the dashpots.

It will be appreciated that the preceding processing method merely illustrates one example of fabrication of the microfluidic system and that other processing methods can be utilized.

The microfluidic system can be used in a variety of applications or devices where it is desirable to regulate fluid flow at a nano-scale, meso-scale, or micro-scale level. In one example of the invention, the microfluidic system can be used as a switch or valve for an assay or lab-on-a chip. In another example, the microfluidic system can be used as pressure sensor for a safety device (e.g., pressure indicators for car seats, switch for air bag actuation, tampering indicator). Still other microfluidic applications include capillary and pressure systems for ink jet printing as well as microfluidic strain gauges.

What has been described above includes examples and implementations of the present invention. Because it is not possible to describe every conceivable combination of components, circuitry or methodologies for purposes of describing the present invention, one of ordinary skill in the art will recognize that many further combinations and permutations of the present invention are possible. Accordingly, the present invention is intended to embrace all such alterations, modifications and variations that fall within the spirit and scope of the appended claims.

Having described the invention, the following is claimed:

1. A flow directing material comprising:
a substrate that includes a first region that exudes fluid in response to a compressive or tensile load and a second region that imbibes fluid in response to the load, the first region having a first porosity and a first permeability, the second region having a second porosity and a second permeability, the first permeability and the second permeability being about $10^{-13}$ m$^2$ to about $10^5$ m$^2$ and the first porosity and the second porosity being 0.3 to about 0.7, the first porosity and the second porosity being at least about 5% different.

2. The flow directing material of claim 1, the first region and the second region extending from a first surface of the substrate, and wherein in response to compressive or tensile load to the substrate, the first region exuding fluid from the first surface toward the direction of the load and the second region imbibing fluid from the first surface away from the direction of the load.

3. The flow directing material of claim 2, the first region including a first fluid, the first fluid flowing from the first region in response to compressive or tensile load.

4. The flow directing material of claim 2, the first surface being in contact with a fluid source, the fluid source being imbibed by the second region in response to the load.

5. The flow directing material of claim 2, the direction of flow of fluid through the first region at the first surface being opposite to the direction of flow of fluid though the second region at the first surface.

6. The flow directing material of claim 1, the first region comprising a first porous polymeric material having a first porosity and the second region comprising a second porous polymeric material having a second porosity different that the first porosity.

7. The flow directing material of claim 1, the first porous polymeric material having a first flexible polymeric foam structure of interconnected open cells and the second porous polymeric material having a second flexible polymeric foam structure of interconnected open cells.

8. The flow directing material of claim 6, the stiffness of the first polymeric material and the second polymeric material determining the penetration depth of the fluid from the first region and to the second region.

9. The flow directing material of claim 1, the first region having a permeability different than the permeability of the second region.

10. The flow directing material of claim 1, further including a porous membrane provided on the first surface to modulate fluid flow through the first surface.

11. The flow directing material of claim 2, the substrate including a second surface substantially opposite to and separated from the first surface, the first region and the second region being laterally spaced in the substrate and extending between the first surface and the second surface.

12. The flow directing material of claim 11, the substrate including a plurality of first regions laterally spaced from one another in the substrate and separated by the second region.

13. The flow directing material of claim 12, at least some of the first regions having a different porosity, volume, volumetric permeability, and/or surface permeability than the porosity, volume, volumetric permeability, and/or surface permeability of other first regions.

14. The flow directing material of claim 1, being provided in at least one of an absorbent article, textile, drug delivery device, bioprosthetic device, biomaterial implant, or microfluidic device.

15. A dressing comprising a substrate that includes a plurality of first regions that exudes fluid in response to a compressive or tensile load and a plurality of second regions that imbibes fluid in response to the load, the first regions having a first porosity and a first permeability, the second regions having a second porosity and a second permeability, the first permeability and the second permeability being about $10^{-13}$ $m^2$ to about $10^5$ $m^2$ and the first porosity and the second porosity being 0.3 to about 0.7, the first porosity and the second porosity being at least about 5% different.

16. The dressing of claim 15, the substrate including a first surface and second surface separated from the first surface, the first regions and the second regions extending between the first surface and the second surface, in response to compressive or tensile load to the first surface, the first region exuding fluid from the first surface toward the direction of the load and the second region imbibing fluid from the first surface away from the direction of the load.

17. The dressing of claim 15, the first region including a therapeutic fluid, the therapeutic fluid flowing from the first regions through the first surface in response to the dressing being under compressive or tensile load.

18. The dressing of claim 17, the therapeutic fluid including at least one pharmaceutical agent, anti-inflammatory agent, antibiotic, antifungal agent, antipathogenic agent, antiseptic agent, hemostatic agents, local analgesics, immunosuppressive agents, growth factor, peptide, or gene therapy agent.

19. The dressing of claim 15, the first regions comprising a first porous polymeric material having a first porosity and the second regions comprising a second porous polymeric material having a second porosity different that the first porosity.

20. The dressing of claim 19, the first porous polymeric material having a first flexible polymeric foam structure of interconnected open cells and the second porous polymeric material having a second flexible polymeric foam structure of interconnected open cells.

21. The dressing of claim 15, further comprising a slip layer attached to the second surface, the slip layer minimizing friction of the outer surface of the dressing when the dressing is applied to the subject.

22. The dressing of claim 15, the second region absorbing excess fluid or exudate from a wound of a subject in response to applying the first surface of the dressing against the wound.

23. The dressing of claim 15, at least some of the first regions having a different porosity, volume, volumetric permeability, and/or surface permeability than the porosity, volume, volumetric permeability, and/or surface permeability of other first regions.

24. The flow directing material of claim 1, wherein the compressive or tensile load is exogenous.

25. The flow directing material of claim 1, wherein the direction of fluid flow out of the first region is opposite to the direction of fluid flow into the second region as a result of the first porosity and the second porosity being at least 5% different.

26. The flow directing material of claim 1, wherein the direction in which the first region exudes fluid and the direction in which the second region imbibes fluid changes as the location of the load on the substrate changes.

27. The flow directing material of claim 1, wherein the first region exudes fluid toward the direction of the load and the second region imbibes fluid away from the direction of the load regardless of the location of the load on the substrate.

28. The flow directing material of claim 1, wherein the flow directing material is adapted for positioning against a wound, the flow directing material having a first surface facing away from the wound, the first region imbibing fluid and the second region exuding fluid in response to applying the compressive or tensile load to the first surface.

29. The dressing of claim 15, wherein the compressive or tensile load is exogenous.

30. The dressing of claim 15, wherein the direction of fluid flow out of the first regions is opposite to the direction of fluid flow into the second regions as a result of the first porosity and the second porosity being at least 5% different.

31. The dressing of claim 15, wherein the direction in which the first regions exude fluid and the direction in which the second regions imbibe fluid changes as the location of the load on the substrate changes.

32. The dressing of claim 15, wherein the first regions exude fluid toward the direction of the load and the second regions imbibe fluid away from the direction of the load regardless of the location of the load on the substrate.

33. The dressing of claim 15, wherein the dressing is adapted for positioning against a wound, the flow directing material having a first surface facing away from the wound, the first region imbibing fluid and the second region exuding fluid in response to applying the compressive or tensile load to the first surface.

* * * * *